US00PP11121P

United States Patent [19]

Osiecki

[11] Patent Number: Plant 11,121

[45] Date of Patent: Nov. 9, 1999

[54] SPATHIPHYLLUM PLANT NAMED 'S18'

[75] Inventor: Marian W. Osiecki, Marianna, Fla.

[73] Assignee: Oglesby Plants International, Inc., Altha, Fla.

[21] Appl. No.: 09/069,928

[22] Filed: Apr. 30, 1998

[51] Int. Cl.[6] ..... A01H 5/00

[52] U.S. Cl. ..... Plt./364

[58] Field of Search ..... Plt./364

[56] References Cited

U.S. PATENT DOCUMENTS

P.P. 8,849 7/1994 Caldwell ..... Plt./364
P.P. 10,748 1/1999 Osiecki ..... Plt./364
P.P. 10,786 2/1999 Osiecki ..... Plt./364

*Primary Examiner*—Lynette R. F. Smith
*Assistant Examiner*—Kent L. Bell
*Attorney, Agent, or Firm*—Rothwell, Figg, Ernst & Kurz

[57] ABSTRACT

A new and distinct cultivar of Spathiphyllum is provided. The plant is medium to large size, full, symmetrical; suitable for production in a 15–25 cm pot from a single tissue culture produced microcutting; maintains proper growth habit and leaf shape at close pot spacing; grows very vigorously; branches early and freely; flowers naturally early and abundantly producing good quality inflorescences from the onset of flowering; has thick, strong peduncles and medium to large spathes with little green coloration, held relatively close to foliage.

2 Drawing Sheets

SUMMARY OF THE INVENTION

This invention relates to a new and distinct Spathiphyllum cultivar characterized by the following combinatin of repeatedly observed traits:

1. Medium to large size,
2. full and symmetrical growth habit,
3. growth habit and leaf shape maintained at crowded pot spacing,
4. very vigorous growth,
5. early and abundant branching,
6. early and abundant natural flowering,
7. good quality inflorescences from the onset of flowering,
8. thick, strong peduncles,
9. medium to large spathes with little green coloration, held relatively close to foliage;

and primarily selected for those characteristics being so selected from the progeny of the cross stated below in a cultivated area near Altha, Fla.

ORIGIN AND ASEXUAL REPRODUCTION

The new cultivar is a product of a planned breeding program carried out at Oglesby Plants International, Inc. near Altha, Fla. The female parent was a selected clone of Spathiphyllum hybrid, 'Bond A', (U.S. Plant Pat. No. 8,849) now marketed as Symphony™ and the male parent was a selected clone of Spathiphyllum hybrid, 'Supreme'®, (patent not applied for). The cross was made in 1991. The plant was selected in 1993 and has since been reproduced by tissue culture in the vicinity of Altha, Fla., with the characteristics stated, found to be maintained through successive generations.

This new cultivar has been identified as Spathiphyllum 'S18'. It is possible that other identification will be adopted in the trade, but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'S18' was approximately 13 months from planting a single tissue culture produced microcutting in a 15 cm pot.

In the photographs:

DETAILED DESCRIPTION OF THE NEW CULTIVAR

Figure 1:
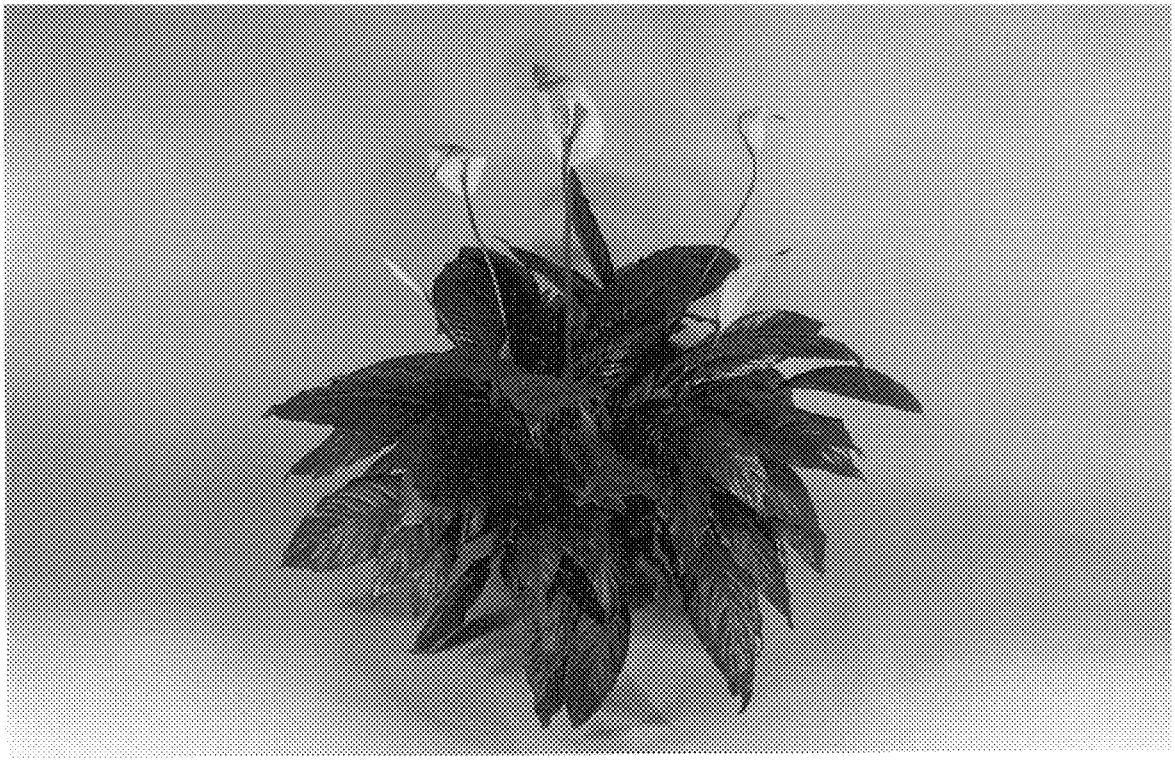
FIG. 1 depicts the whole plant.
Figure 2:
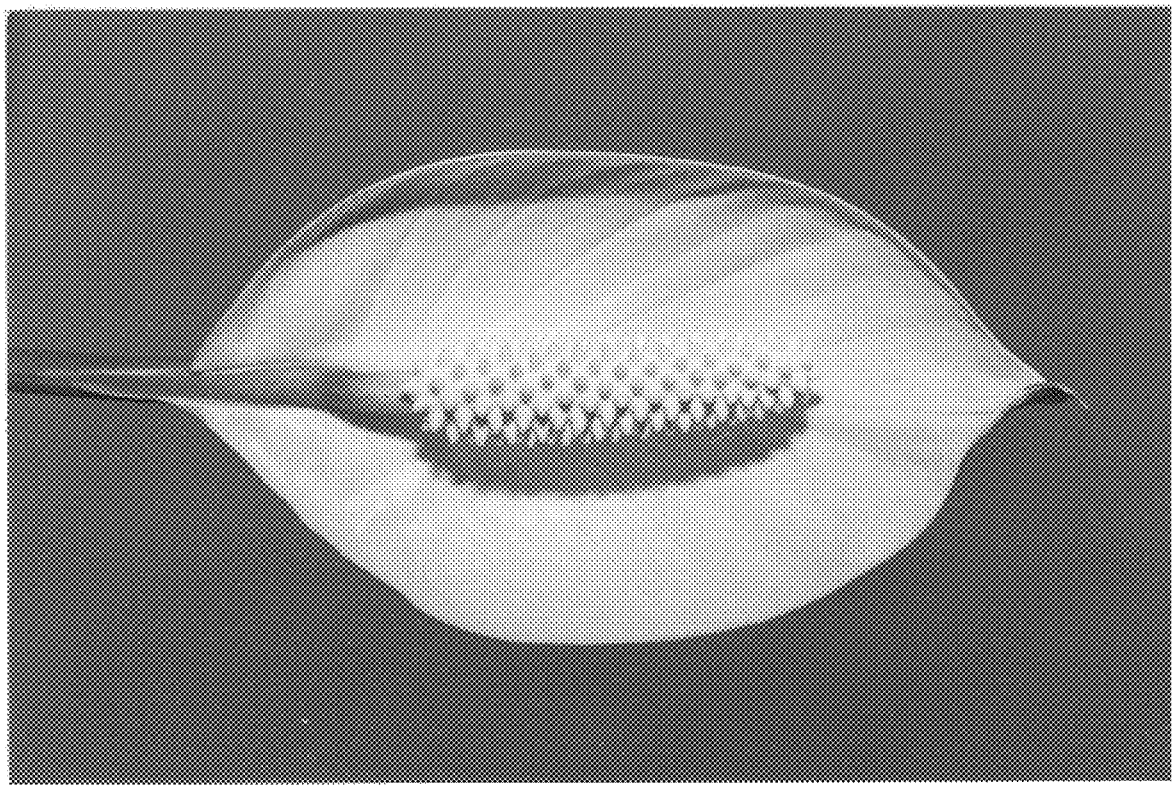
FIG. 2 illustrates the mature inflorescence.
Figure 3:
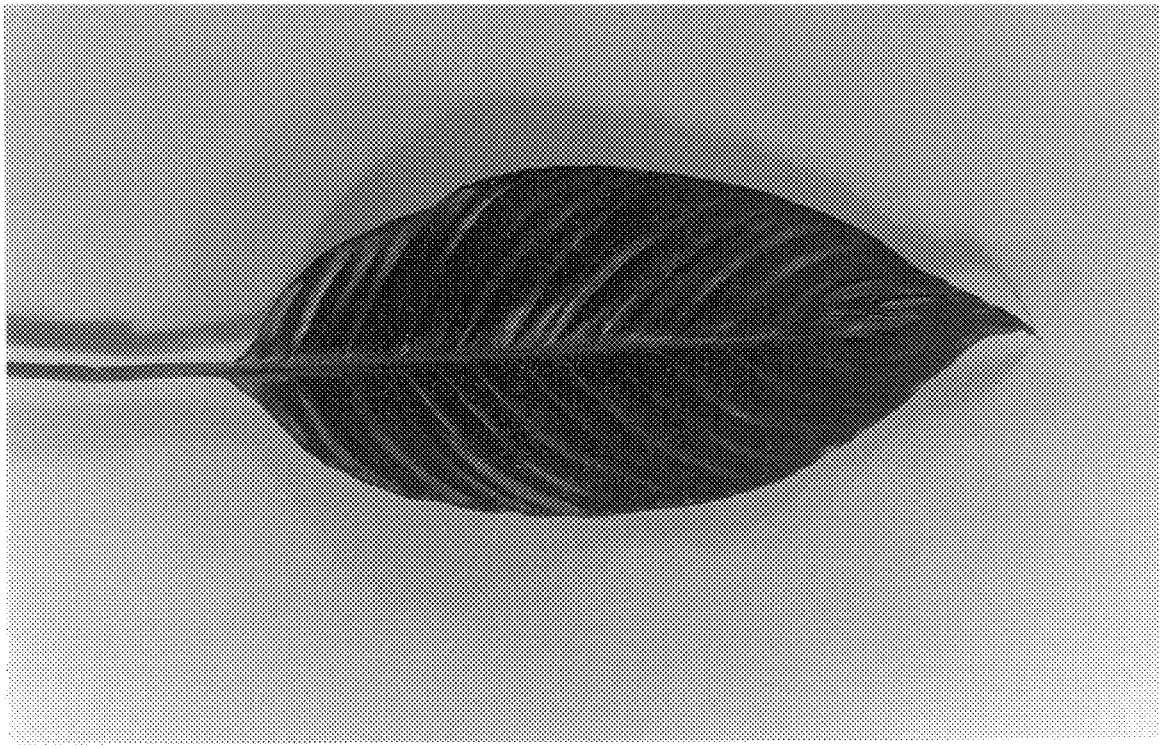
FIG. 3 illustrates the top of a mature leaf.
Figure 4:
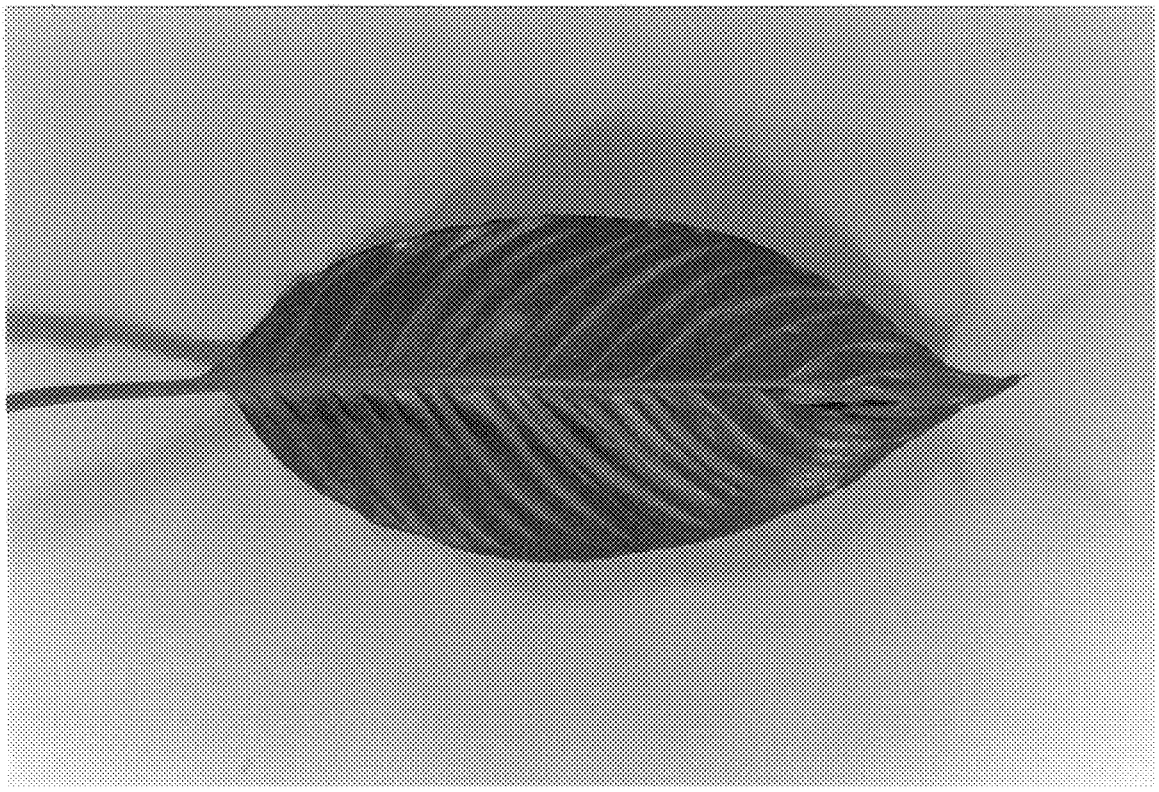
FIG. 4 illustrates the bottom of a mature leaf.

The following observations and measurements describe plants grown in Homestead, Fla., under shade house conditions. These observations and measurements were recorded near Altha, Fla., in December, 1997, from mature plants in 15 cm pots, about 13 months from planting a single tissue culture produced microcutting per pot. Fully developed organs on a dominant stem were used for measurements. Color values were determined on Dec. 2, 1997, under natural, indirect light of approximately 400–500 foot-candles. Color references are made to The R.H.S. Colour Chart, except where general color terms of ordinary significance are used.

'S18' has not been observed under all possible environmental conditions. The phenotype may vary with variations in environment and horticultural practices, such as temperature, light intensity, day length, fertilization, propagation method, etc., without any change in genotype.

Botanical classification: Spathiphyllum hybrid 'S18'.

Parentage:

*Female parent.*—Selected clone of Spathiphyllum hybrid 'Bond A' (U.S. Plant Pat. No. 8,849).

*Male parent.*—Selected clone of Spathiphyllum hybrid 'Supreme'® (patent not applied for).

Propagation: Plant tissue culture.

Plant descriptions:

*Growth habit.*—Medium to large size, full, symmetrical, very well branched with distinct main stem.

*Height.*—Foliage 40–53 cm, with spathes 63–73 cm.
*Width.*—65–77 cm.

Petiole:

*Length.*—Leaf supporting inflorescence: 24.5–27.5 cm long, 4.3–4.6 mm in diameter immediately below geniculum. Geniculum 4.3–5.2 cm long, 4.5–5.6 mm in diameter at the base. Petiole wings 21.0–25.0 cm long. Leaf penultimate to leaf supporting inflorescence: 20.0–26.0 cm long, 4.3–4.8 mm in diameter immediately below geniculum. Geniculum 3.4–4.6 cm long, 5.0–5.3 mm in diameter at the base. Petiole wings 17.0–20.2 cm long.

Leaf blade:

*Shape.*—Elliptic; tip acuminate with some cuspidate tendencies, often slightly curved; base cuneate; margin slightly wavy.

*Size.*—Leaf supporting inflorescense: 23.0–26.3 cm long by 10.3–11.7 cm wide; length: width ratio 2.2–2.4: 1. Leaf penultimate to leaf supporting inflorescense: 24.0–27.5 cm long by 10.6 12.3 cm wide; length: width ratio 2.0–2.4: 1.

*Texture.*—Smooth, glossy.

*Veins.*—Well defined and sunken in the adaxial leaf surface.

*Color.*—Mature Leaf: Adaxial: Darker than 137A (green), usually lighter and more green than 147A (yellow-green). Abaxial: Most Similar to 137C. Newly Unrolled Leaf: Adaxial: Darker and usually more green than 144A (yellow-green). Abaxial: Lighter than 137C.

Inflorescence:

*Arrangement.*—Spathes carried on thick, strong peduncles relatively close to foliage. Ratio spathe length (without wings): spadix length 1.9–2.5: 1.

Peduncle:

*Size.*—54.0–61.5 cm long; 5.4–6.8 mm in diameter immediately below spathe. Stipe 1.7–2.2 cm long, 5.1–6.1 mm in diameter. Peduncles on side shoots sometimes slightly bent.

*Color.*—Front: 144A (yellow-green). Distal zone of stipe 144C–D. Back: 144A or a little lighter with lighter streaks (144C–D), which distally increase in area and dominate the distal zone of stipe.

Spathe:

*Shape.*—Elliptic; tip acuminate, sometimes with some cuspidate tendencies, twisted, usually asymmetric; base cuneate to almost obtuse with long asymmetric wings. Past maturity spathe generally does not lean back. Spathes on side shoots tend to be narrower and have more cuneate bases.

*Size.*—Length (without wings): 12.0–13.7 cm; width: 6.5–7.4 cm; depth: 2.1–2.8 cm. Length: width ratio 1.6–2.1: 1. Wings: 1.8–4.1 cm long and up to 3 mm wide.

*Color.*—Bud: Lighter than 160D (greyed-yellow), darker and more yellow thant 158A (white). Open Spathe: 155A (white) in front and in the back with limited green coloration, confined to the midrib and to the tip. Back: At the juncture with stipe an approximately 4 mm wide band in the midrib is yellow-green (144A) or a little lighter with some lighter streaks (144B–C). The band tapers to slightly over 1 mm around midlength, with edges approximately 144A and the center approximately 144C. In most of distal half, it is a fraction of a mm wide, approximately 144C except for the tip, where it is wider with indistinct borders and darker (resembling 146A–B and 144A). Front: Very fine line is visible in the distal half of the midrib. It becomes wider and darker in the tip — most similar to 146B (yellow-green).

Spadix:

*Size.*—5.5–6.3 cm long; 1.7–2.0 cm in diameter.

*Flower density.*—Perianth visible between pistils. Usually 5 flowers in approximately straight longitudinal line on a 2 cm long middle portion of the spadix.

Botanical flower:

*Size and shape.*—Pistil large, thick, elliptic with some ovate tendencies; tip acute. Stigma relatively small. Mature pistil 5.0–6.0 mm long, protrudes 2.5–3.5 mm beyond perianth, 2.0–3.0 mm in diameter. Stamens not visible before pollen release.

*Color.*—Perianth approximately 158C; pistil approximately 158A–B; stamens approximately 158D (all yellow-white). Pollen approximately 158D (yellow-white) or 159D (orange-white), relatively abundant.

*Roots.*—Main roots thick, fleshy, cream with yellow root caps; abundant fine lateral roots.

Flowering: Flowers naturally in 12.5 cm pots, approximately 8–10 months from planting tissue culture produced microcuttings, producing good quality inflorescences from the onset of flowering. Approximately 13 months from planting a single microcutting two to five white spathes present above foliage in a 15 cm pot.

Spathe longevity: Spathe remains white for up to almost four weeks following bud appearance above foliage and then gradually changes to a green color.

Disease and insect resistance: No known susceptibility to diseases or insects noted to date.

COMPARISON WITH KNOWN CULTIVARS

The new cultivar can be compared to known cultivars 'S2', (U.S. Plant Pat. No. 10,786), now marketed as 'Flower Power' and 'S16', (U.S. Plant Pat. No. 10,748), now marketed as 'Showpiece'.

'S18' is distinguished from both cultivars by its fuller, wider and less upright growth habit; slightly lighter color leaves with more pronounced veins and wavy margins.

'S18' is further distinguished from 'S2' by more abundant branching and smaller spathes, being closer to foliage.

'S18' is further distinguished from 'S16' by the spathes, which generally do not bend back past maturity.

The new cultivar can also be compared to the parent cultivars 'Bond A', (U.S. Plant Pat. No. 8,849), now marketed as 'Symphony' and with 'Supreme' (patent not applied for).

'S18' is distinguished from 'Bond A' by its larger size, more upright growth habit, more vigorous growth, earlier branching, earlier natural flowering, thicker and stronger peduncles, and larger spathes.

'S18' is distinguished from 'Supreme' by its smaller size, fuller, more symmetrical and less upright growth habit better maintained at crowded pot spacing, earlier and more abundant branching, earlier and more abundant natural flowering, smaller leaves, and smaller less round spathes with more green coloration held closer to the foliage.

I claim:

1. A new and distinct cultivar of Spathiphyllum plant named 'S18', substantially as described and illustrated herein, characterized particularly as to novelty by its medium to large size; full and symmetrical growth habit; exceptionally vigorous growth; early and abundant branching; early and abundant natural flowering; medium to large spathes with limited green coloration, held on thick strong peduncles relatively close to foliage.

* * * * *